US012557996B1

(12) United States Patent
Katinas et al.

(10) Patent No.: US 12,557,996 B1
(45) Date of Patent: Feb. 24, 2026

(54) PROCESSING SHORT VIDEO TO OBTAIN FREQUENCY INFORMATION

(71) Applicant: National Technology & Engineering Solutions of Sandia, LLC, Albuquerque, NM (US)

(72) Inventors: Christopher Michael Katinas, Livermore, CA (US); Jerilyn A. Timlin, Albuquerque, NM (US); Thomas A. Reichardt, Pleasanton, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 188 days.

(21) Appl. No.: 18/415,935

(22) Filed: Jan. 18, 2024

(51) Int. Cl.
*A61B 5/024* (2006.01)
*A61B 5/00* (2006.01)
*G06V 40/16* (2022.01)

(52) U.S. Cl.
CPC ........ *A61B 5/02416* (2013.01); *A61B 5/7257* (2013.01); *G06V 40/162* (2022.01)

(58) Field of Classification Search
CPC .............. A61B 5/0077; A61B 5/02416; A61B 2576/00; A61B 5/0013; A61B 5/0022; A61B 5/0205; A61B 5/024; A61B 5/0816; A61B 5/1176; A61B 5/14551; A61B 5/7221; A61B 2503/40; A61B 2560/0475; A61B 5/0006; A61B 5/004; A61B 5/0075; A61B 5/02007; A61B 5/02125; A61B 5/02405; A61B 5/02427; A61B 5/02433; A61B 5/0245; A61B 5/0255; A61B 5/0261; A61B 5/0265; A61B 5/0295; A61B 5/1032; A61B 5/1128; A61B 5/318; A61B 5/33; A61B 5/35; A61B 5/6898; A61B 5/7207; A61B 5/7225; A61B 5/743; A61B 5/746
See application file for complete search history.

(56) References Cited

U.S. PATENT DOCUMENTS

| | | | |
|---|---|---|---|
| 9,336,594 B2 | 5/2016 | Kyal et al. | |
| 9,659,229 B2 | 5/2017 | Clifton et al. | |
| 10,750,959 B2 | 8/2020 | Gupta et al. | |
| 11,083,382 B2 | 8/2021 | Pearce et al. | |
| 11,672,436 B2 | 6/2023 | Balakrishnan et al. | |
| 2015/0313502 A1 | 11/2015 | Mestha et al. | |

*Primary Examiner* — Mark D Remaly
(74) *Attorney, Agent, or Firm* — Calfee, Halter & Griswold LLP; Samantha Updegraff

(57) ABSTRACT

Described are various technologies pertaining to identifying a dominant frequency in an acquired signal, such as a frequency corresponding to a human heartbeat in an acquired video signal. In connection with identifying the dominant frequency, a sub-signal of the acquired signal is extracted from the acquired signal, where the sub-signal includes $N_{samples}$ number of samples (frames). A looped signal is generated by looping the sub-signal. $N_{samples}$ is incremented, and the process is repeated until $N_{samples}$ is equivalent to a predefined threshold; accordingly, numerous looped signals are formed. The dominant frequency is identified based upon the looped signal and presented with the corresponding uncertainty based on harmonic analysis.

9 Claims, 9 Drawing Sheets

1000

102

PROCESSOR

104

MEMORY

1006

INPUT
INTERFACE

1010

106

DATA STORE

OUTPUT
INTERFACE

1012

PROCESSING SHORT VIDEO TO OBTAIN FREQUENCY INFORMATION

STATEMENT OF GOVERNMENTAL INTEREST

This invention was made with Government support under Contract No. DE-NA0003525 awarded by the United States Department of Energy/National Nuclear Security Administration. The U.S. Government has certain rights in the invention.

BACKGROUND

Signal processing involves analyzing analog and/or digital signals, which are processed to remove distortion, mitigate interference, improve signal quality, reduce signal noise, and the like. Signal processing includes subfields such as analog signal processing, digital signal processing, statistical signal processing, and others.

Analog signal processing typically involves electronic circuits such as mixers, filters, integrators, multipliers, voltage-controlled filters and oscillators, as well as phase-locked loops. In contrast, digital signal processing involves digital circuits such as digital signal processors, field-programmable gate arrays, and application-specific integrated circuits.

Statistical signal processing involves stochastic analysis and accounts for statistical properties during signal processing and facilitates modeling noise probability distribution for noise reduction in the signal. Nonlinear signal processing can be used for processing signals from nonlinear systems and can be performed in the time domain, the frequency domain, or the spatio-temporal domain.

Continuous-time signal processing is employed for signals that vary, and can be employed in the time domain, frequency domain, or complex frequency domain. Discrete-time signal processing is employed for sampled signals that occur in discrete points in time.

When analyzing signals, identification of an uncertainty range for an identified frequency value is a problem that has not been satisfactorily addressed by conventional approaches.

SUMMARY

The following is a brief summary of subject matter that is described in greater detail herein. This summary is not intended to be limiting as to the scope of the claims.

Described herein are various technologies pertaining to identifying dominant frequencies in an acquired signal, and more specifically to generating a looped signal comprising sampled frames of the acquired signal to probabilistically identify a dominant frequency.

In one embodiment, the acquired signal is a video signal. A processor is configured to execute computer-executable instructions stored in a memory to analyze the acquired signal and identify dominant frequencies that correspond to one or more parameters associated with a subject in the acquired video signal. The processor is configured to sample the acquired signal at a desired rate and generate a looped signal comprising an initial number of sampled frames $N_{min}$, where the sample frames are looped to form a looped signal that includes M frames (i.e., the looped signal includes the frames 1 through $N_{min}$, 1 through $N_{min}$, 1 through $N_{min}$, . . . ). The looped signal includes discontinuities between adjacent $N_{min}$ samples in the looped signal. The discontinuities generate harmonics that are employed in connection with identifying dominant frequencies in the acquired signal. A Fast Fourier Transform (FFT) is performed on the looped signal, and dominant frequencies and their associated spectral power information are identified and stored. The number of sampled frames $N_{min}$ is then incremented, so that a new looped signal comprising looped $N_{min}+1$ frames is generated, and the FFT and dominant frequency and spectral power information identification and storage are reiterated with respect to the new looped signal. The processor increments the number of sampled frames $N_{samples}$ from $N_{min}$ (the initial number of samples used for the first looped signal) and reiterates the foregoing steps continues until a looped signal of a desired length comprising looped $N_{max}$ samples has been generated and analyzed. $N_{min}$ can be on the order of tens, hundreds, thousands, millions, billions, etc., samples, and $N_{max}$ is greater than $N_{min}$.

Once the Q (where $Q=N_{max}-N_{min}$) looped signals have been generated and analyzed, the processor calculates harmonic frequencies induced by the discontinuities in the looped signals, based on $N_{samples}$, for each of the looped signals.

The processor generates a frequency signature from the looped signals that includes information related to the parameter to be identified. When spectral power is at a minimum (e.g., a trough), the spectral power jumps to a next harmonic where it decreases along the harmonic until the next spectral power trough. When spectral power is at a maximum (e.g., a peak), the frequency value of the frequency signature as it decreases along the given harmonic is identified and stored. This peak analysis is performed for each harmonic. The processor identifies a frequency value on the harmonic associated with the spectral power peak of the highest magnitude as the dominant frequency representative of the parameter to be identified and outputs the dominant frequency value along with a range of uncertainty. That is, the dominant frequency value on the harmonic associated with the highest spectral power peak is identified as the dominant frequency having the highest probability of correctness and is output along with the uncertainty range associated with that harmonic. The uncertainty range has an upper bound defined by a line that runs through the spectral power peaks for the harmonics and a lower bound defined by a line that runs through the spectral power troughs.

In one embodiment, the parameter to be identified is the heart rate of a human subject in the acquired video signal. The processor performs facial recognition on the subject to identify pixels representative of skin on the face of the subject and performs an analysis to identify micro changes in the color of the identified pixels. The frequency signature identified in the looped signals represents micro changes in the color of the identified pixels that correspond to heartbeats.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
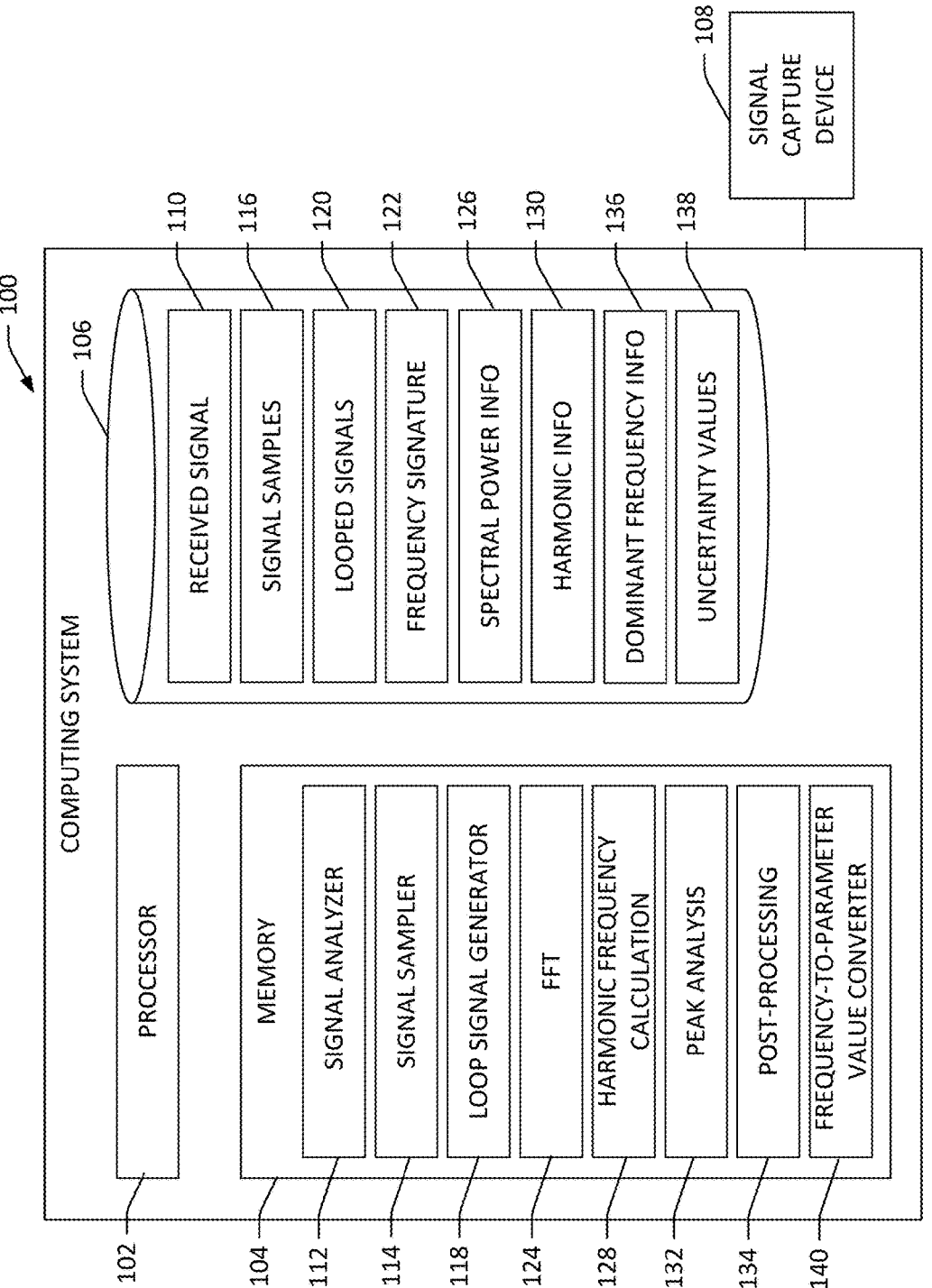
FIG. 1 illustrates a computing system that is configured to identify a dominant frequency in a looped signal.

Various technologies pertaining to frequency-based analysis are now described with reference to the drawings, wherein like reference numerals are used to refer to like elements throughout. In the following description, for purposes of explanation, numerous specific details are set forth to provide a thorough understanding of one or more aspects. It may be evident, however, that such aspect(s) may be practiced without these specific details. In other instances, well-known structures and devices are shown in block diagram form to facilitate describing one or more aspects. Further, it is to be understood that functionality that is carried out by certain system components may be performed by multiple components. Similarly, for instance, a component may be configured to perform functionality that is carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "module," and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Described herein are various technologies related to analyzing frequency content in an acquired signal to identify and quantify a dominant frequency in the acquired signal by looping samples of the acquired signal. In an example, the signal is a video signal.

In wavelet-based frequency analysis, a cone of interest (COI) is defined to describe regions where the analysis results can be trusted; however, once outside the COI, there is no indication of how uncertain the results are. An analytical technique is described herein to identify uncertainty in a signal containing a frequency of interest (e.g., a dominant frequency) to be identified. The algorithm starts with a minimal number of consecutive samples from an original signal (e.g., red-green-blue (RGB) video or other signal containing frequency content, such as thermal or infrared video, audio, lidar, radar, sonar, hyperspectral, etc.) and loops the consecutive samples to generate a substantially longer signal (e.g., multiple times longer than the original signal). This new signal contains two frequencies: (1) a frequency associated with a jump which is inherent upon recycling a subsection of the original signal, and (2) the frequency of interest (i.e., the dominant frequency). Of the two frequencies, the former can be determined from the sampling frequency and the number of samples used to generate the new signal (e.g., harmonic frequency of the discontinuity). Once the new signal is generated, a Fast Fourier Transform (FFT) is performed to obtain the dominant frequency and the corresponding power level of that frequency. It should be noted that the length of the new signal affects the sharpness of the peaks obtained from the FFT, making signal extension relevant. The frequency where the highest power level is observed from the FFT is recorded, along with the power level. Analysis is continued by iteratively adding one additional sample of the original signal and repeating the process: signal extension, FFT analysis, and post-processing. In one embodiment, this process is continued until the full signal is being utilized to generate a new extended signal. The power level and dominant frequency from each of the FFTs is then analyzed to identify the maximum power level, which is explained within a given harmonic band (thus, defining the dominant frequency). Uncertainty bounds are derived as a function of the number of samples used to construct the looped signal, as the range of potential dominant frequencies within a particular harmonic band define the corresponding uncertainty.

With reference now to FIG. 1, a computing system 100 that is configured to identify a dominant frequency in a looped signal is illustrated. The computing system 100 includes a processor 102, memory 104, and a data store 106. The data store 106 includes data that is accessible to the processor 102, and the memory 104 includes data that is accessible to the processor 102 and instructions that are executed by the processor 102. The computing system 100 is coupled to a signal capture device 108 (e.g., a video camera, an audio recorder, a radar system, a lidar system, thermal imaging device, infrared imaging device, hyperspectral imaging device or any other device suitable for capturing signal containing frequency content).

In one embodiment, the signal capture device 108 is a video camera (e.g., a red-green-blue (RGB) camera or the like) that captures video of a scene (e.g., a hospital environment such as a waiting room or the like, a gym or fitness facility, a patient on a video conference with a healthcare provider, a sports venue, an airport, a train station, etc.). A signal analyzer component 112 stored in the memory 104 is executed by the processor 102 and is configured to analyze the acquired signal 110. The signal analyzer component 112 analyzes the acquired signal 110 to identify components within the signal that can be analyzed using frequency-based analysis. The acquired signal is sampled by a signal sampler component 114 which generates signal samples 116 at a predefined sampling rate (e.g., 30 Hz, 40 Hz, or some other predefined sampling rate). The processor 102 executes a loop signal generator component 118, which generates looped signals 120 in the manner set forth below.

The minimum number of frames used in the looped signal is based on the frequency to be identified. In one example, the sampling rate can be set to 30 Hz or higher to mitigate aliasing while being sufficient to identify, e.g., a heart rate of 1 Hz. One of skill in the art will understand that other sampling rates may be used.

In one embodiment, the sampling frequency is set to be at least 10 samples per cycle of the frequency being identified, i.e., an order of magnitude higher frequency than the frequency being identified. Once a sequence of samples is obtained, the sequence of samples is looped to make a longer signal, the duration of which is dependent upon the frequency to be identified. In one example, the looped signal is on the order of seconds, minutes, or longer.

The signal analyzer component 112 analyzes each of the incremented looped signals to identify a frequency signature 122 therein. In one embodiment, the signal analyzer component 112 performs facial recognition on a video signal to identify facial skin on a subject and analyzes the skin pixels. The signal analyzer component 112 can identify pixel intensities representing the subject's facial skin in each frame and can create a bounding box that defines the head of the subject. The signal analyzer component 112 calculates the mode of the pixels in the bounding box, which represents the number of skin pixels in a given video frame. The signal analyzer component 112 can isolate skin pixels by perturbing the mode value by, e.g., 25 pixel intensities (or some other number of pixel intensities) in each color channel, in each direction (higher or lower), to create a signature for the face. The signal analyzer component 112 calculates the average intensity values of the skin pixels, (even when subject is moving), detects the face, and calculates the average value of each of the color channels for analysis. RGB video has three color channels, and there is a linear combination of the three-color channels that provides the highest sensitivity to heartbeat frequency, as will be understood by one of skill in the art. The signal analyzer component 112 generates a single channel signal on which the signal analysis component 112 performs frequency analysis.

The processor 102 executes a Fast Fourier Transform (FFT) component 124 on each of the incremented looped signals 120 to generate spectral power information 126 for the looped signals. The sharpness of the spectral power peaks is a function of the number of samples in the looped video signal (e.g., a one-minute video sampled at 30 Hz has 1800 samples). If the looped signal is extended to 5 minutes, the peaks will be 5 times sharper.

The processor 102 also executes a harmonic frequency calculation component 128 that calculates harmonic frequency bands or harmonic information 130 in the looped signal based on the number of samples $N_{samples}$ in the looped signal and the overall length of the looped signal.

The processor 102 executes a peak analysis component 132, which identifies peaks in the spectral power waveform 126. A post-processing component 134 is executed by the processor to identify dominant frequencies 136 in the frequency signature 122. The frequency signature 122 decreases along a given harmonic line for a number of looped samples before jumping to the next harmonic when spectral power is at a minimum. When spectral power is at a maximum (a peak), the frequency of the frequency signature 122 is identified as a dominant frequency 136 for the given harmonic. The spectral power level (e.g., the spectral power peak) at which the dominant frequency is identified is also noted and stored.

As the looped signals are incremented (by one or more samples of the acquired signal) and get longer, a range of uncertainty for the dominant frequencies becomes narrower. The range of uncertainty has an upper bound defined by the frequency signature peaks and a lower bound defined by the frequency signature troughs. The processor 102 stores in the database 106 uncertainty values and/or ranges 138 for each dominant frequency. The foregoing features are described in greater detail with regard to FIG. 6.

Once a dominant frequency 136 with a highest spectral power peak (e.g., after the first harmonic for having too large an uncertainty range) is identified for output as having the highest probability of correctness among the respective dominant frequencies identified along the respective harmonics, the processor 102 executes a frequency-to-parameter converter component 140 that converts the dominant frequency identified for output to a value per unit time. For instance, if the parameter is a heart rate in beats per minute (BPM), then a dominant frequency of, e.g., 1.3 Hz can be multiplied by 60 to produce an output parameter value of 78 BPM. In another example, the measured parameter is respiratory rate, and a dominant frequency of, e.g., 0.17 Hz can be multiplied by 60 to produce an output parameter value of 10.2 breaths per minute. It will be understood that the foregoing examples are illustrative in nature and not limited to physiological parameter values and/or a 60-second time unit. Rather, the measured parameter may be any desired parameter that can be measured from frequency content in the acquired signal, over any desired time unit (e.g., seconds, minutes, hours, days, months, years, or more, etc.).

According to an example, the parameter associated with the dominant frequency to be identified is, e.g., a heart rate or some other physiological parameter that can be measured from the frequency content of a received signal 110 to identify a person or subject in distress. Taking heart rate as an example, frames from the acquired video can be used for remote sensing of physiological parameters. For instance, from several or many meters away with an RGB video camera capturing video at 30-50 Hz, the system can image a human subject from afar and detect minute color changes of the skin under certain illumination scenarios. Frequency content associated with the subject's heart rate at, e.g., 0.001 to 5 meters or further can be analyzed using the described frequency-based analysis.

The human heart rate is not always constant, even at rest. It is constantly varying, which can be indicative of certain health conditions. Therefore, it becomes desirable to assess in near real-time an error tolerance for the captured frequency content based on shorter and shorter videos. In order to quantify a level of uncertainty associated with the detected signature, assuming an infinitely long video for the sake of example, the signal sampler component 114 can parse out the video into segments, and the FFT component 124 can perform a FFT on each segment. With a video of sufficient length, the underlying frequency signatures in the video can be obtained, one of which corresponds to the heart rate of the subject. However, in practice, a video of several minutes can suffice to permit identification of all dominant frequencies. When this is not available, a video of just a few seconds can be sampled to detect the dominant frequency associated with the heart rate of the subject.

According to an example, assume 10 seconds of video are available. The loop signal generator loops the 10 second signal six times to generate a 60 second looped signal, with identifiable "jumps" in transitions between segments (i.e., the 10-second segments) to create frequency content in the looped signal. At ¹⁄₁₀ Hz (i.e., every 10 seconds), a "jump" is generated in the looped signal that can be identified in the looped signal as frequency content. The discontinuities induce harmonics in the underlying video. Because the original video length (10$s$) and the length of the target video (1 minute) are known, the harmonic order associated with the jumps can be determined by the harmonic frequency calculation component 128. When the FFT component 124 calculates the FFT of the signature (i.e., the average signal of the video), a magnitude is identified that is a function of the length of the video used.

Figure 2:
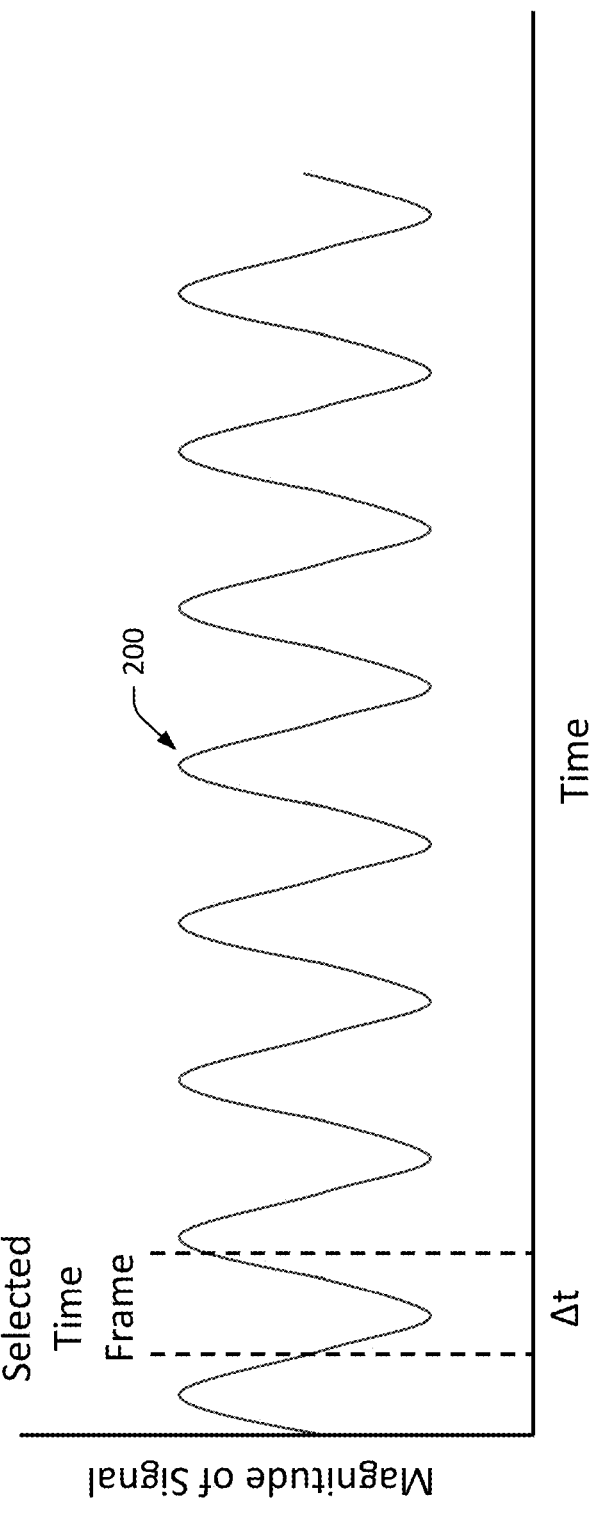
FIG. 2 illustrates an acquired video signal sine wave, wherein a selected time frame (Δt) is less than one period of the sine wave.

FIG. 2 illustrates an acquired video signal sine wave 200, wherein a selected time frame (Δt) is less than one period of the sine wave 200. When the sampling period (time frame Δt) is too short, the frequency content is governed by the discontinuity (see FIG. 3) where the looping occurs.

Figure 3:
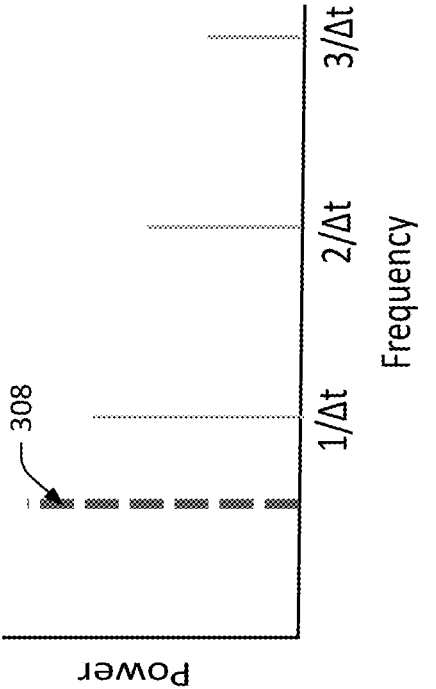
FIG. 3 shows a looped signal comprising samples that are less than one period of the video signal, with discontinuities and an example of the corresponding spectral power.
Figure 3:
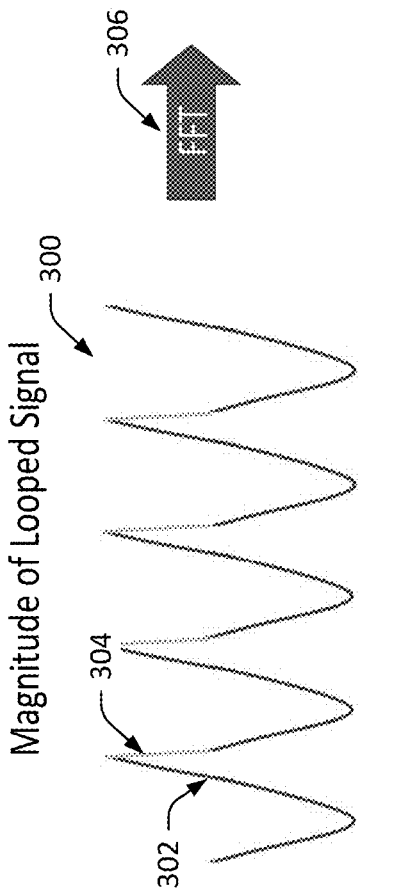

FIG. 3 shows a looped signal 300 comprising samples 302 that are less than one period of the parameter of interest in the video signal, with discontinuities 304 that occur because the samples are not a complete sine wave (i.e., the samples are not a full integer multiple of the sampled signal period). Upon execution of an FFT 306 on the discontinuous signal 300, a dominant frequency 308 can be identified. However, in this example the dominant frequency is not aligned with a harmonic frequency (1/At, 2/At, 3/At, etc.) because the sampling period is too short. Moreover, the dominant frequency is within the first harmonic, where the range of uncertainty is relatively large (see FIG. 6), making the identified value untrustworthy.

Figure 4:
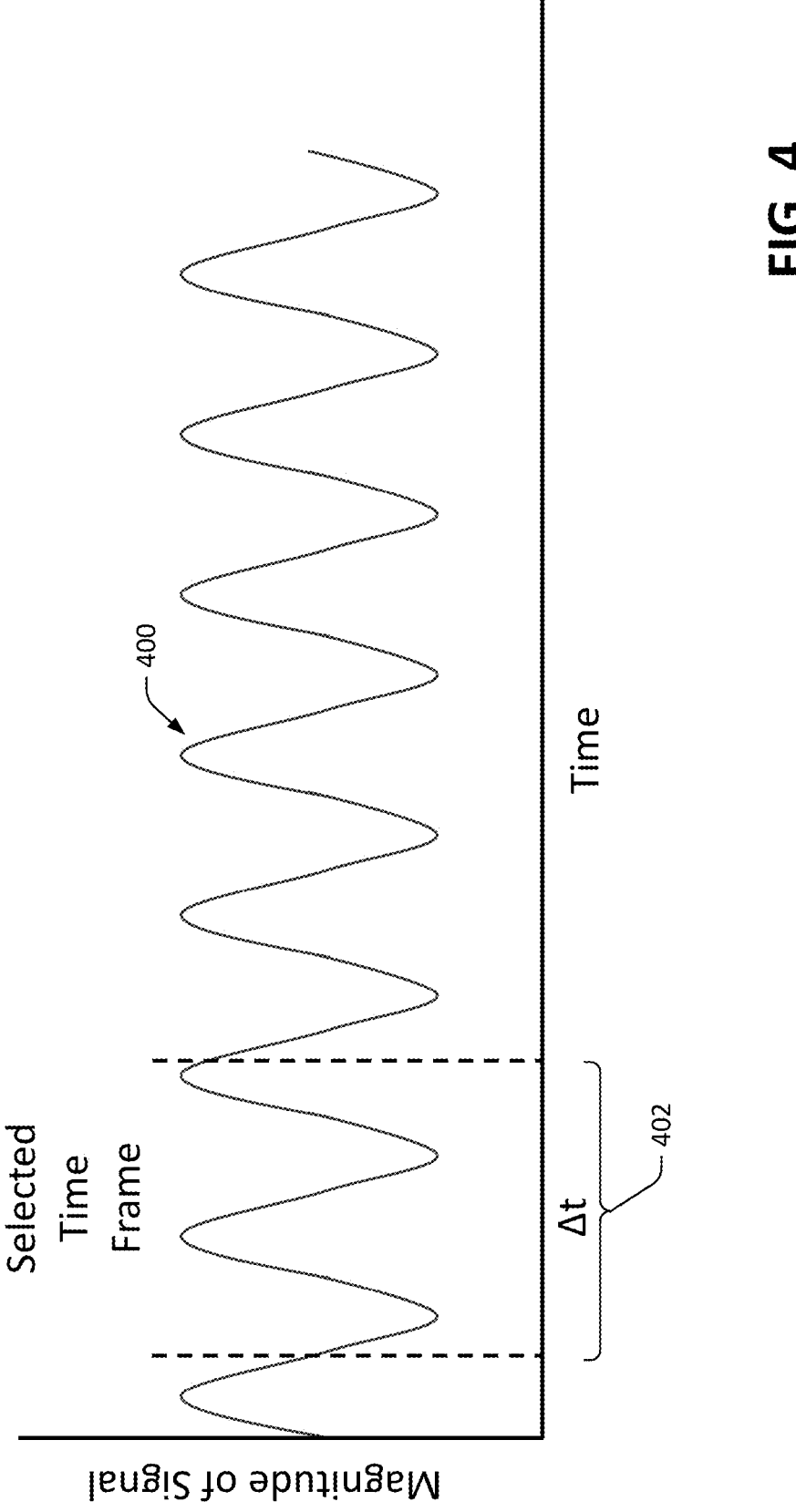
FIG. 4 illustrates an acquired video signal sine wave, wherein a selected time frame (Δt) is greater than one period of the acquired signal.

FIG. 4 illustrates an acquired video signal sine wave 400, wherein a selected time frame (Δt) 402 is greater than one period of the parameter of interest in the acquired signal but less than two full periods. As the sampling period is increased, the power level of the harmonic closest to the actual dominant frequency increases. It will be understood that the time frame can be more than two full periods of the parameter of interest in the acquired signal, more than three full periods of the acquired signal, etc., and that the described techniques are not limited to the sampling period of FIG. 4

Figure 5:
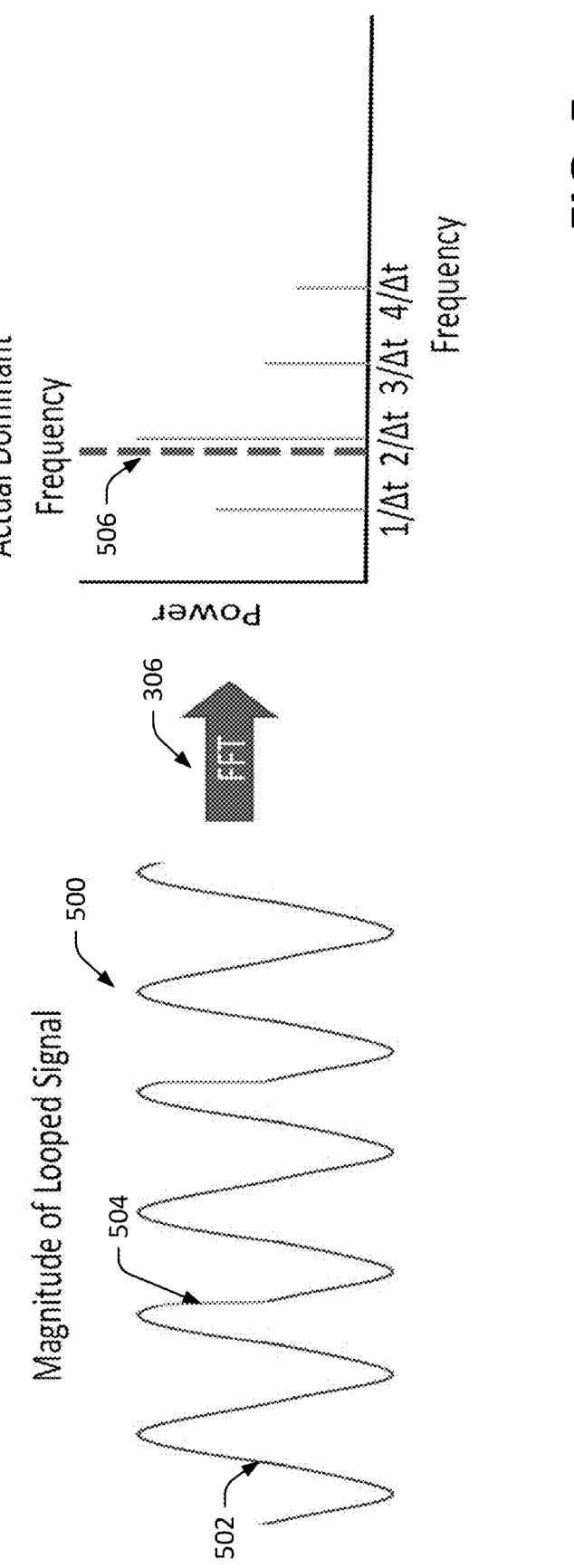
FIG. 5 illustrates a looped signal comprising samples that are longer than one period of the acquired signal.

FIG. 5 illustrates a looped signal 500 that comprises samples 502 that are longer than one period of the parameter of interest in the acquired signal. It will be noted that the samples are less than two full periods long so that discontinuities 504 are introduced in the looped signal. The sample can be longer than two full periods. The discontinuities 504 induce harmonics in the transformed signal upon an FFT being applied over the looped signal. The absolute power level is maximized when the dominant frequency 506 is nearly coincident with the harmonic frequency. In the example of FIG. 5, the actual dominant frequency 506 is coincident with the second harmonic at 2/At, which has the highest spectral power according to this example.

Figure 6:
FIG. 6 illustrates a graph showing a frequency signature as it correlates to spectral power and harmonic.

FIG. 6 illustrates a graph 600 showing a frequency signature 602 as it correlates to spectral power 604 and harmonic frequencies as a function of a number of samples used to generate a looped signal. In the illustrated example, the looped signal was analyzed using an FFT starting at a 20-sample signal through a 200-sample signal for a total of 181 rounds of iteration, wherein each looped signal is 1 sample longer than the previous looped signal. In an example where the signal is a video signal, the first looped signal is generated from 20 video frames, the second looped signal is generated from 21 video frames, and so on until the 181$^{st}$ looped signal is generated from 200 video frames. It will be understood that the numbers used in this example are illustrative in nature and not to be construed in a limiting sense. Rather, the looped signal may start with any number of video frames (e.g., greater than 3) and be extended to any desired number of video frames.

The frequency signature of the detected frequency (left axis of 600), 602 exhibits a quasi-sawtooth pattern such that the frequency signature 602 decreases along a given harmonic frequency (labeled 1$^{st}$ through 10$^{th}$ in the illustrated example) until spectral power is at a minimum, and then jumps to a higher harmonic frequency. It will be understood that more or fewer harmonic frequencies may occur depending on the number of samples used. The jumps between harmonic frequencies are shown as vertical lines 606 in the frequency signature 602. As the frequency signature 602 decreases along a given harmonic, a dominant frequency 608 is identified where spectral power is at a maximum (i.e., a peak) for that harmonic. For each harmonic, a dominant frequency is identified. In FIG. 6, dominant frequencies 608 are indicated by pentagrams on each harmonic coincident with a spectral power peak.

At the left-hand side of the graph 600, the frequency signature follows the first harmonic. A dominant frequency representing, e.g., heart rate of a subject in the video can be detected along the first harmonic but may not be a reliable value considering the large uncertainty range between an upper uncertainty bound 610 and a lower uncertainty bound 612. The upper uncertainty bound 610 represents a boundary that passes through the peaks of the frequency signature across harmonics, and the lower uncertainty bound represents a boundary that passes through the troughs of the frequency signature. The uncertainty range of a dominant frequency detected on the first harmonic can be on the order of 50 to 80 beats per minute, and thus a dominant frequency detected on the first harmonic may not be reliable. Therefore, the looped signal is iteratively extended so that the frequency signature jumps to the second harmonic, the third harmonic, the fourth harmonic, and so on. Within each harmonic, a point on the frequency signature that corresponds to the highest spectral power for that harmonic denotes the heart rate with the most certainty within that harmonic. It will be understood that the values described herein are presented by way of example and are not to be construed in a limiting sense with regard to the value of the uncertainty in the first harmonic.

The jumps in the frequency signature between harmonics create uncertainty and are larger between the lower harmonic numbers. For higher harmonics (e.g., the 2$^{nd}$ through the 8$^{th}$), a mean heart rate of 78 beats per minute is detected in this example. As can be seen, the longer the looped video signal, the narrower the uncertainty range becomes. In this manner, uncertainty range can be determined based on the number of samples used.

In one embodiment, dominant frequencies having an uncertainty range that is larger than a predetermined threshold range are excluded from selection for output. The predetermined threshold range can be a percentage above and below the dominant frequency, a number of Hz above and below the dominant frequency, etc., and the upper and lower bounds of the uncertainty range may be, but need not be, an equal distance from the dominant frequency in percentage or Hz.

Figure 7:
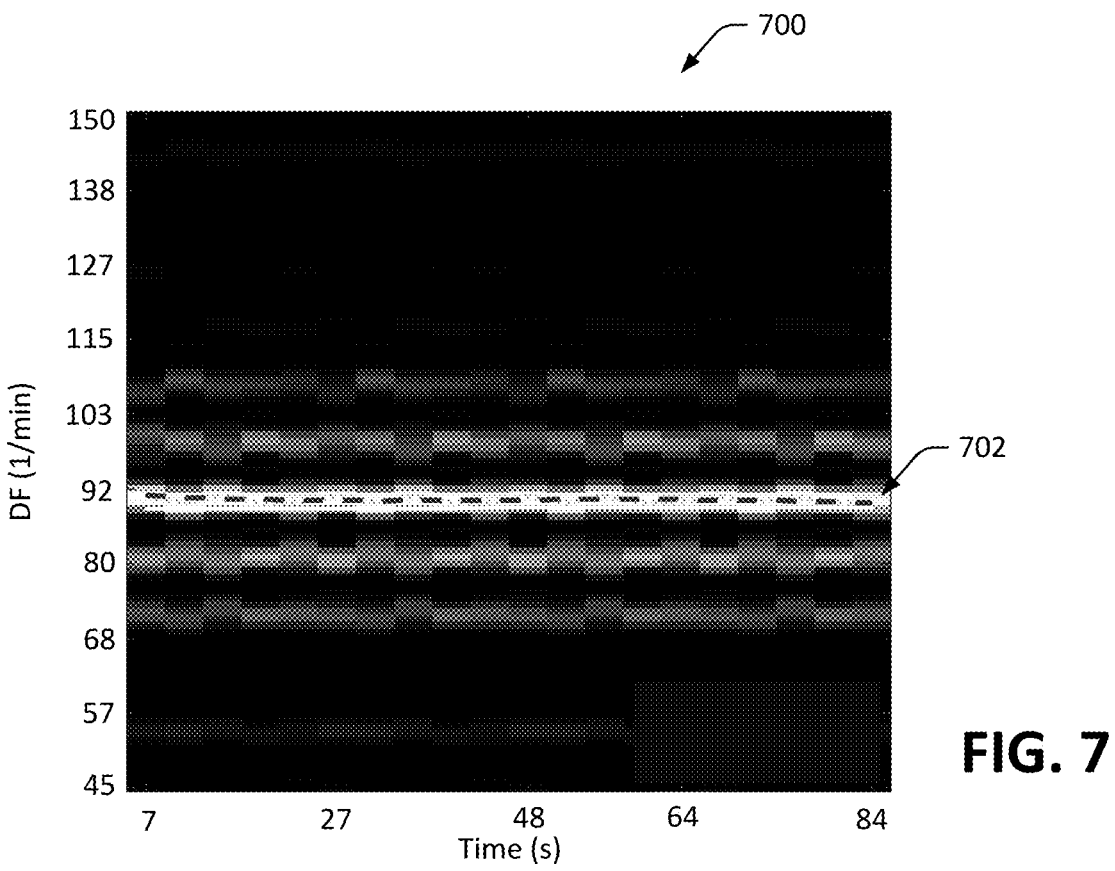
FIG. 7 shows a frequency analysis correlating dominant frequency and time using a looped video signal.

FIG. 7 shows a periodogram 700 correlating dominant frequency and time, using a looped video signal generated in accordance with the aspects described herein. A dominant frequency 702 is shown at approximately 90 beats per minute. Other bands are visible at approximately 70 beats per minute, 80 beats per minute, 100 beats per minute, and 110 beats per minute. These bands are present because the analyzed video was looped with discontinuities that induced harmonics. The band at 90 beats per minute is the brightest band because it has the highest spectral power, and therefore is the dominant frequency with the highest probability of being the subject's actual heart rate.

Figure 8:
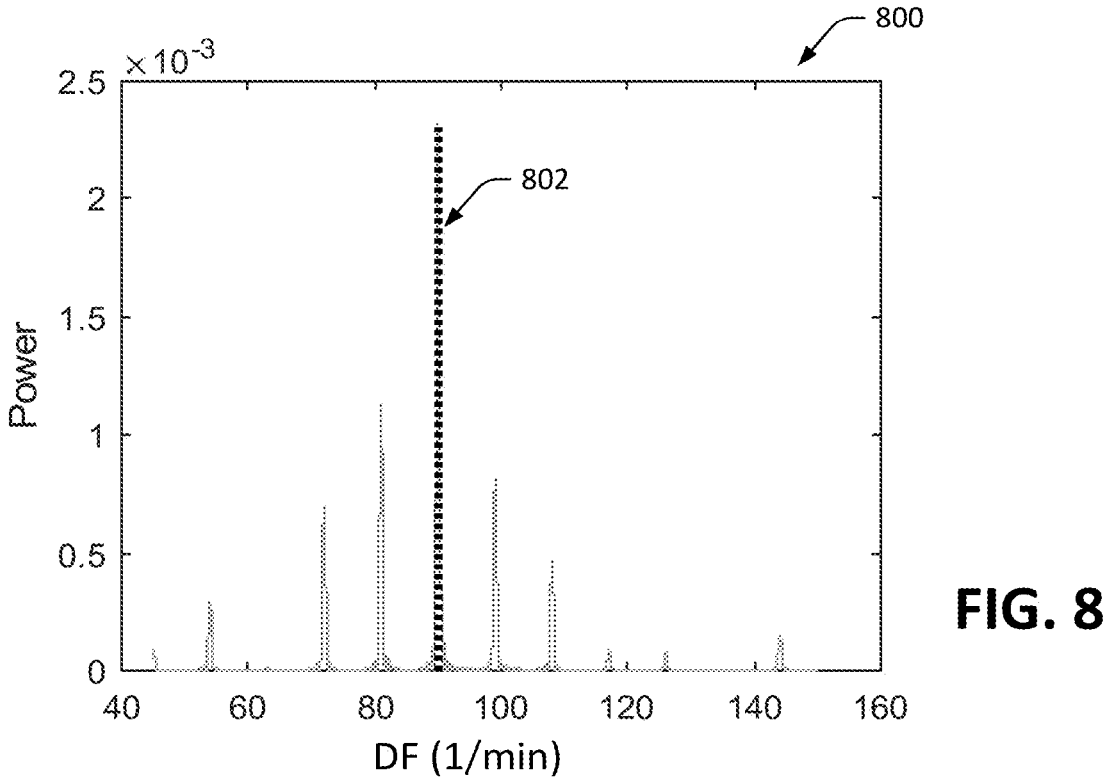
FIG. 8 is a spectrogram showing the correlation between dominant frequency and power for the various harmonics for a looped video signal.

FIG. 8 is a spectrogram 800 showing the correlation between dominant frequency and power for the various harmonics for a looped video generated as described herein. As can be seen, the highest spectral power 802 is associated with a dominant frequency at approximately 90 beats per minute coincident with the $6^{th}$ harmonic, while the maximum power for the other detected frequencies is much lower.

Figure 9:
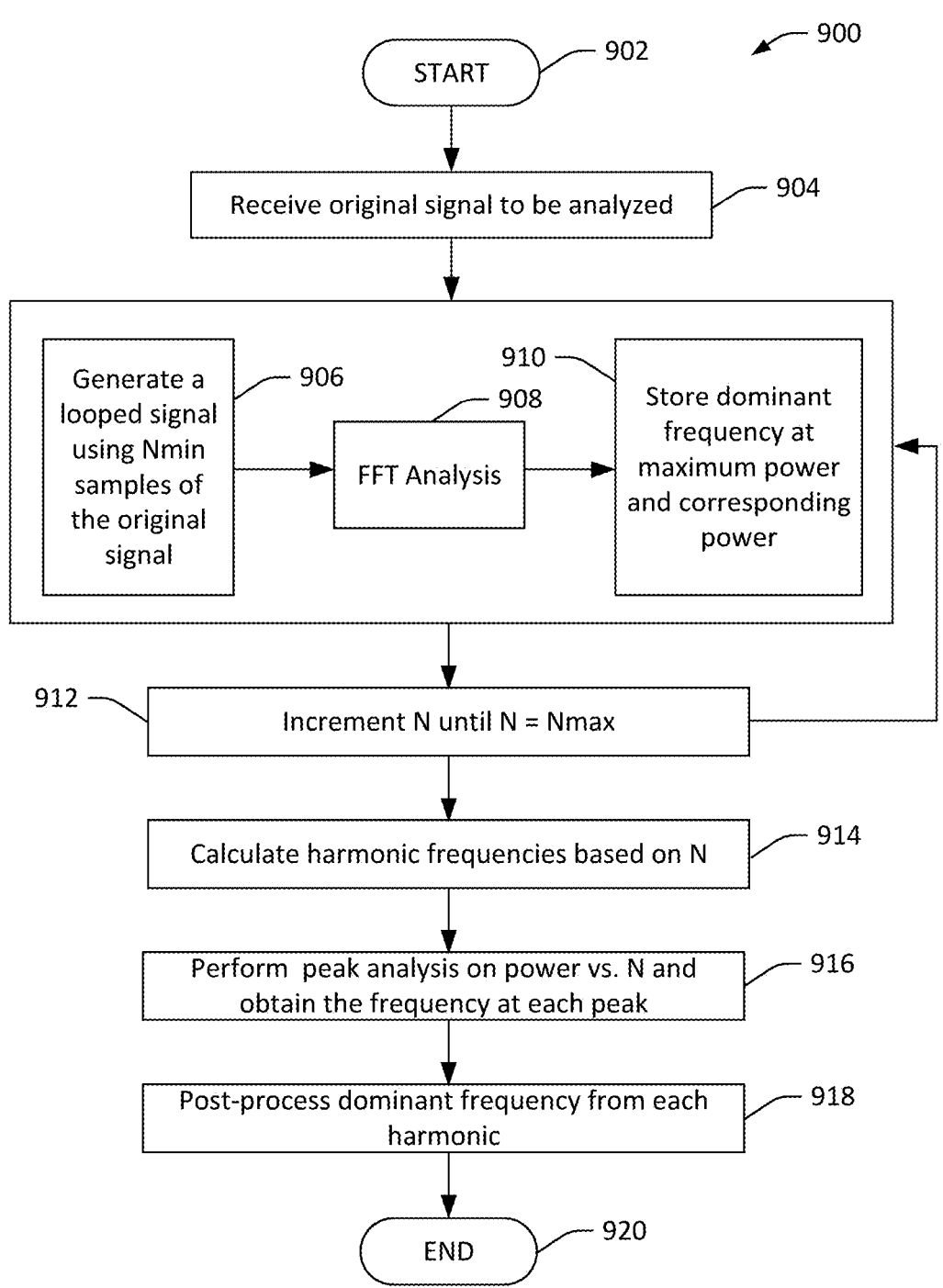
FIG. 9 illustrates a method for identifying dominant frequencies in an acquired signal using discontinuous looped samples of the signal and spectral power analysis.

FIG. 9 illustrates a method relating to identifying dominant frequencies in an acquired signal using looped samples of the signal and spectral power analysis. While the method is shown and described as being a series of acts that are performed in a sequence, it is to be understood and appreciated that the method is not limited by the order of the sequence. For example, some acts can occur in a different order than what is described herein. In addition, an act can occur concurrently with another act. Further, in some instances, not all acts may be required to implement a method described herein.

Referring solely to FIG. 9, a method 900 is illustrated for determining a dominant frequency in a signal having frequency content. The method begins at 902. At 904, a signal is obtained for analysis. At 906, a looped signal is generated using the first $N_{samples}$ of the acquired signal. For instance, the signal can be sampled at a selected frequency, and the first $N_{samples}$ are stitched together to generate the looped signal. At 908, fast Fourier transform analysis is performed on the looped signal. At 910, the dominant frequency at maximum power and the corresponding maximum power at which the dominant frequency occurs are recorded.

Acts 906, 908, and 910 are performed iteratively as $N_{samples}$ is incremented through a desired number of samples at 912. According to an example presented in FIG. 6, in a first iteration $N_{samples}$ may be set to 20 so that the first looped signal comprises $N_{min}$ segments (or some other value, e.g., 20 segments, 100 segments, 1000 segments, etc.) of the acquired signal stitched together. On the next iteration of acts 906, 908, and 910, the looped signal comprises 21 segments, and so on until $N_{samples}$ equals a desired number of segments $N_{max}$ segments (e.g., 200 segments or some other selected number of segments that is greater than $N_{min}$). In this example, with $N_{samples}$ ranging from 20 to 200, acts 906, 908, and 910 would be iterated 181 times. At, e.g., 30 Hz sampling rate, the length of the 181 looped signals ranges from 0.66 seconds to 6.66 seconds. It will be understood that the foregoing sampling rate, and $N_{min}$ and $N_{max}$ values are illustrative in nature and are not intended to be construed in a limiting sense.

At 914, harmonic frequencies for the looped signals are calculated based on $N_{samples}$ for the respective looped signals. At 916, peak analysis is performed on the stored power levels versus $N_{samples}$, and the frequency at each peak is obtained. In one embodiment, a single value is obtained for each harmonic. At 918, the dominant frequency from each harmonic is post-processed to quantify a parameter associated with the dominant frequency. The method terminates at 920.

Figure 10:
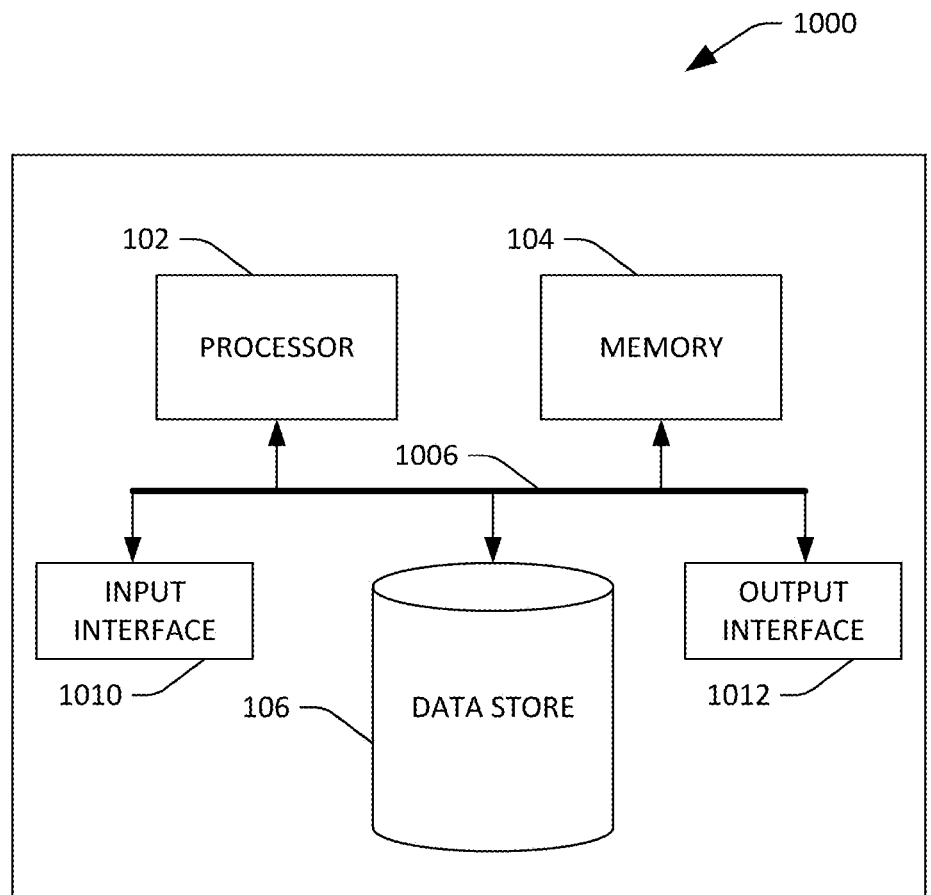
FIG. 10 is a high-level illustration of an exemplary computing device.

Referring now to FIG. 10, a high-level illustration of an exemplary computing device 1000 that can be used in accordance with the systems and methodologies disclosed herein is illustrated. For instance, the computing device 1000 may be used in a system that identifies dominant frequencies in an acquired signal and calculates a range of uncertainty therefor. The computing device 1000 includes the processor 102 that executes instructions that are stored in the memory 104. The instructions may be, for instance, instructions for implementing functionality described as being carried out by one or more components discussed above or instructions for implementing one or more of the methods described above. The processor 102 may access the memory 104 by way of a system bus 1006.

The computing device 1000 additionally includes the data store 106 that is accessible by the processor 102 by way of the system bus 1006. The data store 106 may include information, etc., as described with regard to FIG. 1. The computing device 1000 also includes an input interface 1010 that allows external devices to communicate with the computing device 1000. For instance, the input interface 1010 may be used to receive instructions from an external computer device, from a user, etc. The computing device 1000 also includes an output interface 1012 that interfaces the computing device 1000 with one or more external devices. For example, the computing device 1000 may display text, images, etc. by way of the output interface 1012.

It is contemplated that the external devices that communicate with the computing device 1000 via the input interface 1010 and the output interface 1012 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1000 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1000 may be a distributed system. Thus, for instance, several devices may be in communication by way of a network connection and may collectively perform tasks described as being performed by the computing device 1000.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionality described herein can be performed, at least in part, by one or more hardware logic components. For example, and without limitation, illustrative types of hardware logic components that can be used include Field-programmable Gate Arrays (FP-GAs), Application-specific Integrated Circuits (ASICs), Application-specific Standard Products (ASSPs), System-on-a-chip systems (SOCs), Complex Programmable Logic Devices (CPLDs), etc.

Various technologies are described herein in accordance with at least the following examples.

(A1) In an aspect, a method for identifying a dominant frequency in a signal having frequency content is disclosed herein. The method includes receiving a signal, where the signal is based upon output of a signal capture device. The method also includes extracting a sub-signal from the acquired signal, where the sub-signal comprises $N_{samples}$ samples. The method further includes generating a looped signal based upon the sub-signal, where the looped signal comprises several instances of the sub-signal appended to one another. The method additionally includes incrementing $N_{samples}$ by at least one sample and repeating the extracting, generating, and processing acts until $N_{samples}=N_{max}$, wherein $N_{samples}$ ranges from $N_{min}$ to $N_{max}$, wherein $N_{max}$ is greater than $N_{min}$, and further where Q looped signals are generated. The method also includes identifying a dominant frequency in the acquired signal based upon the Q looped signals and outputting the identified dominant frequency with uncertainty bounds.

(A2) In some embodiments of the method of (A1), the method also includes calculating dominant frequencies for each looped signal based on $N_{samples}$ for the looped signal, wherein the dominant frequencies are identified based upon harmonic numbers.

(A3) In some embodiments of the method of (A2), the method further includes for each looped signal, identifying a respective looped dominant frequency, where the dominant frequency is identified from amongst the looped dominant frequencies for the looped signals.

(A4) In some embodiments of the method of (A3), the looped dominant frequencies are identified based upon spectral power analysis performed with respect to the looped signals.

(A5) In some embodiments of the method of at least one of (A1)-(A4), the acquired signal is a video signal.

(A6) In some embodiments of the method of (A5), the dominant frequency is representative of a heartbeat rate of a subject in the video signal.

(A7) In some embodiments of the method of at least one of (A1)-(A6), the method also includes performing an FFT on each of the Q looped signals. The method further includes identifying and storing dominant frequencies and spectral power levels at which the respective dominant frequencies occur, where the dominant frequency is identified based upon the stored dominant frequencies and the spectral power levels.

(A8) In some embodiments of the method of at least one of (A1)-(A7), the method additionally includes computing an uncertainty range for the identified dominant frequency based upon the Q looped signals.

(A9) In some embodiments of the method of at least one of (A1)-(A8), the acquired signal is a video signal that includes a human subject. The method also includes prior to sampling, performing facial recognition on the human subject in the acquired video signal. The method further includes identifying skin pixels in frames of the video signal, where the Q looped signals are based upon the identified skin pixels, and further where the identified dominant frequency is representative of heart rate of the human subject.

(B1) In another aspect, a system that facilitates identifying a dominant frequency in a signal having frequency includes a processor and memory, where the memory stores instructions that, when executed by the processor, cause the processor to perform any of the methods disclosed herein (e.g., any of the methods of (A1)-(A9)).

(C1) In yet another aspect, a computer-readable storage medium includes instructions that, when executed by a processor, cause the processor to perform any of the methods disclosed herein (e.g., any of the methods of (A1)-(A9)).

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates identifying a dominant frequency in a signal having frequency content, comprising:
   a processor; and
   memory storing instructions that, when executed by the processor, cause the processor to perform acts comprising:
   receiving a signal, where the signal is based upon output of a signal capture device;
   extracting a sub-signal from the acquired signal, where the sub-signal comprises $N_{samples}$ samples of the acquired signal;
   generating a looped signal based upon the sub-signal, where the looped signal comprises several instances of the sub-signal appended to one another;
   incrementing $N_{samples}$ by at least one sample and repeating the extracting, generating, and processing acts until $N_{samples}=N_{max}$, wherein $N_{samples}$ ranges from $N_{min}$ to $N_{max}$, wherein $N_{max}$ is greater than $N_{min}$, and further where Q looped signals are generated;
   identifying a dominant frequency in the acquired signal based upon the Q looped signals; and
   outputting the identified dominant frequency with uncertainty bounds.

2. The system of claim 1, the acts further comprising:

calculating dominant frequencies for each looped signal based on $N_{samples}$ for the looped signal, wherein the dominant frequencies are identified within respective harmonic numbers.

3. The system of claim 2, the acts further comprising:

for each looped signal, identify a respective looped dominant frequency, where the dominant frequency is identified from amongst the looped dominant frequencies for the looped signals.

4. The system of claim 3, where the looped dominant frequencies are identified based upon spectral power analysis performed with respect to the looped signals.

5. The system of claim 1, where the acquired signal is a video signal.

6. The system of claim 5, where the dominant frequency is representative of a heartbeat rate of a subject in the video signal.

7. The system of claim 1, the acts further comprising:

performing an FFT on each of the Q looped signals; and identifying and storing dominant frequencies and spectral power levels at which the respective dominant frequencies occur, where the dominant frequency is identified based upon the stored dominant frequencies and the spectral power levels.

8. The system of claim 1, the acts further comprising:

computing an uncertainty range for the identified dominant frequency based upon the Q looped signals.

9. The system of claim 1, wherein the acquired signal is a video signal that includes a human subject, the acts further comprising:

prior to sampling, performing facial recognition on the human subject in the acquired video signal; and identifying skin pixels in frames of the video signal, where the Q looped signals are based upon the identified skin pixels, and further where the identified dominant frequency is representative of heart rate of the human subject.

\* \* \* \* \*